United States Patent [19]

Carey et al.

[11] Patent Number: 5,691,400
[45] Date of Patent: Nov. 25, 1997

[54] COMPOSITIONS

[75] Inventors: John Gerard Carey, Warrington; John Christopher Padget, Frodsham; David Alan Pears, Chester, all of United Kingdom

[73] Assignee: Zeneca Limited, London, England

[21] Appl. No.: 440,136

[22] Filed: May 12, 1995

[30] Foreign Application Priority Data

May 12, 1994 [GB] United Kingdom .................. 9409543

[51] Int. Cl.$^6$ ............................... C08K 3/20; C08L 63/02
[52] U.S. Cl. ........................... 523/404; 428/413; 523/409
[58] Field of Search ..................... 523/404, 409; 428/413

[56] References Cited

U.S. PATENT DOCUMENTS 3,555,051  1/1971  Marsden et al. .
4,330,446  5/1982  Miyosawa ................................. 523/409

FOREIGN PATENT DOCUMENTS 0540812  5/1993  European Pat. Off. .
0562283  9/1993  European Pat. Off. .
2269780  11/1990  Japan .

OTHER PUBLICATIONS

Database Chemical Abstracts Host:STN Abstract 115: 73 694, see abstract & JP A 02 269 780 (Kansai Paint Co.) 5 Nov. 1990.

RN 138249–34–0–CA 116(5):41762g.
RN 130570–76–2–CA 118(12):103840h.
RN 130570–76–2–CA 114(6):44226e.
RN 130570–76–2–CA 113(24):213293m.
RN 130570–76–2–CA 93:79310.
RN 130570–75–1–CA 114(6):44226e.
RN 130570–75–1–CA 113(24):213293m.
RN 130570–75–1–CA 93:79310.
RN 97794–71–3–CA 103(12):88782k.
RN 36805–67—1–CA 77(22):140906q.
RN 26739–05–9–CA 72(18):91448c.
RN 24942–73–2–CA 72 (18):91448c.
RN 24942–67–4–CA 72 (18):91448c.
RN 24704–76–5–CA 71(16):71740t.
RN 24704–75–4–CA 71(16):71740t.

*Primary Examiner*—Melvyn I. Marquis
*Assistant Examiner*—David Aylward
*Attorney, Agent, or Firm*—Cushman Darby & Cushman IP Group Pillsbury Madison & Sutro LLP

[57] ABSTRACT

A composition comprising water and the following components:
(a) an epoxy compound comprising at least one epoxy group and at least one hydrolysable silyl group; and
(b) a hydroxy functional polymer having carboxy and/or sulpho groups.

The compositions are generally water-based and may be used for making films and coatings having good mechanical and physical properties.

11 Claims, No Drawings

COMPOSITIONS

The present invention relates to crosslinkable aqueous coating compositions containing a specified epoxy compound and a polymer having a hydroxy group and a carboxy and/or sulpho group.

Industrial coatings are prepared to protect and decorate underlying materials. Originally, these coatings were primarily organic solvent-borne systems, but the development of water-borne coatings has become of increasing interest for a number of reasons. The main reasons for the shift from organic solvent-borne coatings to aqueous alternatives is to decrease the amount of organic solvent emitted into the atmosphere.

In the development of water-borne coatings it has become apparent that the quality of the coating performance is often inferior to that of solvent-borne coatings. It is known that to improve the properties of the aqueous coating the components of the composition need to be designed such that they react and cross-link with the binder on the substrate. Because of the temperature sensitive nature of many of the substrates it is preferred that such compositions will undergo effective cross-linking at ambient temperatures without the need for catalysts, particularly toxic catalysts. We have now devised a highly effective water-based crosslinkable coating composition which can give films and coatings having good mechanical and physical properties.

According to the present invention there is provided a composition comprising water and the following components:

(a) an epoxy compound comprising at least one epoxy group, at least one nitrogen atom selected from amino, amido and urea nitrogen atoms, and at least one hydrolysable silyl group; and (b) a hydroxy functional polymer having carboxy and/or sulpho groups.

The epoxy compound preferably has from 1 to 10, more preferably from 1 to 6, epoxy groups. The epoxy groups are alicyclic or preferably aliphatic. In alicyclic epoxy groups the carbon atoms of the epoxy ring form an alicyclic ring, preferably 5-, 6-, or 7-membered (for example a cyclopentane or cyclohexane ring), whereas in aliphatic epoxy groups the carbon atoms of the epoxy ring form an aliphatic chain. Examples of aliphatic epoxy groups are shown below in (i) and (ii) and alicyclic epoxy groups are shown in (iii) and (iv).

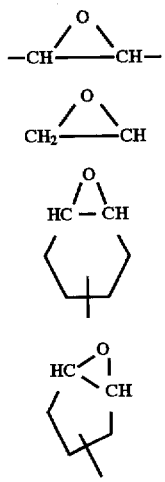

Component (a) contains at least one nitrogen atom, selected from amino, amido and urea nitrogen atoms. Each nitrogen atom which may be present in component (a) is preferably that of a secondary amino group, and more preferably that of a tertiary amino group because the epoxy compounds having tertiary amino groups are generally more storage stable. When the a nitrogen atom is that of a secondary amino group it is preferred that the epoxy group (s) is or are 5-, 6- or 7-membered alicyclic rings because these tend robe more storage stable than compounds wherein the epoxy group is aliphatic. The pKa of each nitrogen atom preferably lies in the range 1 to 12, more preferably 5 to 11.

We have found that when the epoxy group in component (a) has an ester group (i.e. —O—C(=O)—) on an adjacent carbon atom then component (a) is a more effective crosslinker for component (b) in terms of the speed and extent of crosslinking. This improvement is particularly marked when the epoxy group is an aliphatic epoxy group.

Examples of epoxy groups having an ester group on an adjacent carbon atom are shown in formulae (V), (VI), (VII) and (VIII) below:

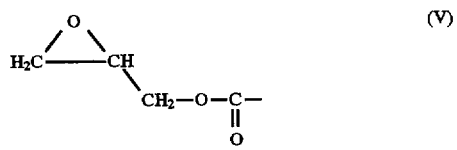

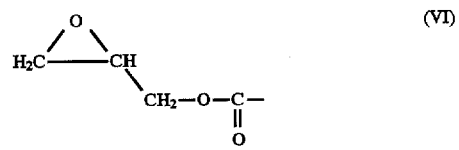

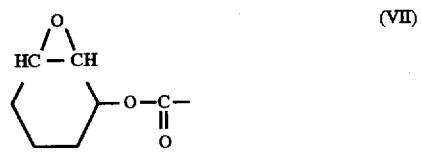

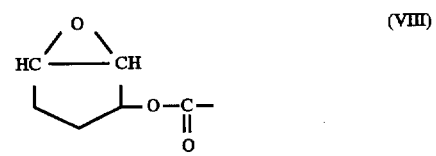

It is preferable that component (a) has at least 1 or 2 hydrolysable silyl group. A hydrolysable silyl group is a group which is convertible to a hydroxysilyl group on treatment with aqueous acid or base. A preferred hydrolysable silyl group is of the formula —Si($R^1$)$_3$ wherein each $R^1$ independently is optionally substituted alkyl (especially $C_{1-4}$-alkyl) or optionally substituted alkoxy (especially $C_{1-4}$-alkoxy or a poly(oxyalkylene)), provided at least one $R^1$ is optionally substituted alkoxy. Preferably all three groups represented by $R^1$ are $C_{1-4}$-alkoxy. When one, two or three of the $R^1$ groups are optionally substituted alkoxy groups the hydroxysilyl groups obtainable from the hydrolysable silyl group are respectively of formula —SiOH, —Si(OH)$_2$ and —Si(OH)$_3$ wherein the remaining valencies of Si are taken up by the other $R^1$ groups. Examples of hydrolysable silyl groups include each of —Si(OCH$_3$)$_3$, —Si(OCH$_3$)$_2$CH$_3$, —Si(OCH$_2$CH$_3$)$_3$ and —Si(OCH$_2$CH$_3$)$_1$[O(CH$_2$CH$_2$O)$_2$CH$_3$]$_2$, the latter containing two poly(oxyethylene) groups.

Component (a) is preferably water-soluble or, more preferably, water-dispersible. Water-solubility and water-dispersibility may be achieved by the presence of sulpho, carboxy or poly(oxyalkylene) groups (especially poly(oxyethylene) and poly(oxypropylene) groups). The poly(oxyalkylene) groups are preferably attached to the silicon atom in the hydrolysable silyl group in component (a) or, if present, to the nitrogen atom.

A preferred epoxy compound which may be used as component (a) is of the Formula (1):

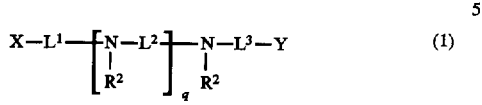

wherein:

X is E—$(L^4$—O$)_m$—(CO$)_n$—(T$)_p$—;

Y is —Si $(R^1)_3$ as hereinbefore defined;

T is O, $CH_2$ or $NR^R$;

P is 0 or 1;

q is 0, 1, 2, 3 or 4;

E comprises an epoxy group;

each $L^1$, $L^2$, $L^3$ and $L^4$ independently is a divalent organic linker group;

m and n are each independently 0 or 1; and each $R^2$ independently is H, —$L^1$X or optionally substituted alkyl or acyl.

When q is 2, 3 or 4 each $L^2$ and each $R^2$ may be the same or different.

In a preferred epoxy compound of Formula (1), m=n=q=1; p=0; $L^1$, $L^2$, $L^3$ and $L^4$ are optionally substituted alkylene groups containing from 1 to 6 carbon atoms (especially —$CH_2$—, —$(CH_2)_2$— or —$(CH_2)_3$—); Y is —Si $(R^1)_3$ wherein each $R^1$ independently is optionally substituted alkyl (especially $C_{1-4}$-alkyl) or optionally substituted alkoxy (especially $C_{1-4}$-alkoxy or a poly(oxyalkylene)), provided at least one $R^1$ is optionally substituted alkoxy; E is of formula (ii), (iii) or (iv) (especially of formula (ii)); and one group represented by $R^2$ is of formula —$L^1$—X wherein $L^1$ and X are as hereinbefore defined (with the preferences for E, $L^4$, m, n and p as above) and the other group represented by $R^2$ is H, optionally substituted alkyl or acyl (especially H or —CONH($C_{1-20}$-alkyl), more especially H or —CONH($C_{1-4}$-alkyl)).

An especially preferred compound of Formula (1) is that which has q=1 and $L^2$=$(CH_2)_2$, which reduces to the formula:

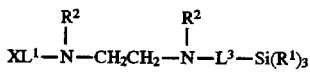

wherein $L^3$ has the meaning given above, each $R^1 L^3$ has the meaning given above, independently is $C_{1-4}$-alkyl or $C_{1-4}$-alkoxy, provided at least one $R^1$ is $C_{1-4}$-alkoxy; and wherein further $R^2$ is H, —$L^1$X, or —CO($C_{1-4}$-alkyl) and the other $R^2$ is —$L^1$X wherein X has $L^4$=$CH_2$, m=1 and E is of formula (ii) and $L^1$ is $(CH_2)_2$, which reduces —$L^1$X to the formula:

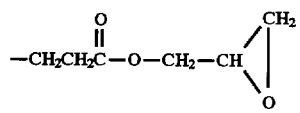

A second preferred class of epoxy compound is of Formula (2):

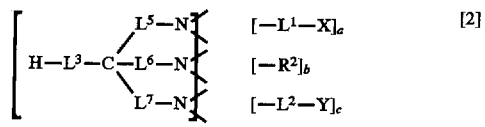

wherein:

$L^1$, $L^2$, $L^4$, X, and Y are as hereinbefore defined;

$R^2$ is H or optionally substituted alkyl or acyl;

$L^5$, $L^6$ and $L^7$ are each independently organic linker groups;

a is 1 to 5;

b is 0 to ¼;

c is 1 to 5; and (a+b+c)=6.

E is preferably of formula (ii), (iii) or (iv) shown above.

The divalent organic linker groups are preferably optionally substituted alkylene, arylene or aralkylene. Preferred optionally substituted alkylene groups contain from 1 to 6 carbon atoms, more preferably 1 to 4 carbon atoms. A preferred optionally substituted arylene group is phenylene. A preferred optionally substituted aralkylene group contains from 7 to 10 carbon atoms, especially benzylene. The optional substituents which maybe present on the divalent organic linker groups are preferably methyl, amino, ether, hydroxy or ester groups. The divalent organic linker groups may contain or be free from hetero linking atoms, for example ether or thioether groups.

Examples of preferred groups represented by $L^1$, $L^2$, $L^3$, $L^4$, $L^5$, $L^6$ and $L^7$ include —$CH_2$—, —$(CH_2)_2$—, —$(CH_2)_3$—, —$(CH_2)_4$—, —$CH_2$—CHOH—$CH_2$—, —$CH_2$—CH(OCO$CH_2$CO$CH_3$)—$CH_2$—, —$CH_2CH_2$(O$CH_2CH_2$)$_{1or2}$—, —$CH_2$(O$CH_2$CH($CH_3$))$_{1or2}$—, —C($CH_2CH_3$)(X)—$CH_2$OCH(OH)—$CH_2$— (wherein X is as hereinbefore defined), —$(CH_2)_4$OCH(OH)$CH_2$— and phenylene.

Compounds of Formula (1) wherein n is 1 form a further feature of the invention. Preferably m and n are both 1. Preferably p is 0.

In Formulae (1) and (2) when $R^2$ is optionally substituted alkyl it is preferably alkyl which is unsubstituted or substituted by a poly(oxyalkylene) group, an epoxy group and/or by a hydrolysable silyl group. $R^2$ may also be of formula —$L^1$—X wherein X and $L^1$ are as hereinbefore defined. When $R^2$ is acyl it may be of the formula —CO($C_{1-4}$-alkylene)—CONH($C_{1-4}$-alkyl), —CONH($C_{1-6}$-alkyl) or —CO($C_{1-4}$-alkylene)—CO ($C_{1-4}$-alkyl).

When $R^2$ is H in formula (1) the —$NR^2$—group is a secondary amino group, and when $R^2$ is optionally substituted alkyl —$NR^2$—is a tertiary amino group.

Components (a) and (b) are each independently dissolved or dispersed in the water. Thus the composition maybe an aqueous dispersion or solution. "Aqueous dispersion" means a dispersion of a component in an aqueous carrier medium of which water is the principal component (usually at least 40 or 55 weight % of the carrier medium). Minor amounts of organic liquid(s) maybe present if desired or required. Typically, component (b) will be in the form of an aqueous latex.

Compositions of the invention cross-link well to give film coatings having good mechanical properties and chemical resistance and some have low toxicity. The cross-linking maybe performed at ambient temperatures without using toxic catalysts. If desired one may use a catalyst to speed up cross-linking still further. Suitable catalysts include secondary and tertiary amines, especially triethylamine and tributylamine.

It is preferred that a substrate is coated using the composition of the present invention by applying the composition to a substrate, drying at ambient temperature and ageing the coating so formed at ambient temperature e.g. to develop crosslinking in the coating.

The invention also provides a process for forming a film or coating on a substrate comprising applying thereto a composition according to the invention and allowing water to evaporate therefrom, for example at a temperature of 10° C. to 30° C., or above 30° C. and below 250° C.

The weight ratio of component (a) to component (b) preferably lies in the range 0.1:100 to 35:100, more preferably 0.5:100 to 25:100, especially 1:100 to 15:100.

Component (b)

For the avoidance of doubt, three classes of hydroxy functional polymers having carboxy and/or sulpho groups fall within the definition of component (b), namely:

hydroxy functional polymers having carboxy groups;
hydroxy functional polymers having sulpho groups; and
hydroxy functional polymers having carboxy and sulpho groups.

The choice of hydroxy functional polymer having carboxy and/or sulpho groups used as component (b) will depend upon the properties required for the crosslinable composition. Component (b) preferably has a number average molecular weight of from 100 or 500 to 500,000. Preferably component (b) has an average of at least 1 hydroxy group per molecule, more preferably at least 2. Polyesters, polyurethanes and olefinic polymers are preferred, provided they are hydroxy functional and have a carboxy and/or sulpho group.

As component (b) there maybe used an addition polymer or a condensation polymer, preferably formed by pelymerisation of monomers which provide hydroxy and carboxy and/or sulpho groups in the resultant polymer with monomers which do not contain these groups.

The addition polymer is preferably formed by a free radical polymerisation process, preferably using a mixture of olefinically unsaturated hydroxy functional monomers and olefinically unsaturated carboxy and/or sulpho functional monomers and olefinically unsaturated monomers which are free from hydroxy, sulpho and carboxy groups.

In the free-radical initiated polymerisation methods one may use an olefinically unsaturated hydroxy functional monomer, for example N-methylol (meth)acrylamide and hydroxy-$C_{2-8}$-alkyl esters of (meth) acrylic acid such as hydroxyethyl (meth)acrylate, hydroxypropyl (meth)acrylate and adducts of the aforementioned esters with lactones such as ε-caprolactone, delta-valero lactone etc, and mixtures thereof.

Preferred olefinically unsaturated carboxy functional monomers include olefinically unsaturated carboxylic acids, more preferably mono- and dicarboxylic acids, especially those having 3 to 5 or 6 carbon atoms, more especially acrylic acid, methacrylic acid, fumaric acid, itaconic acid and β-carboxyethyl acrylate (β-CEA).

Preferred olefinically unsaturated sulpho functional monomers are olefinically unsaturated sulphonic acids, more preferably mono- and di-sulphonic acids, especially those having 3 to 5 carbon atoms, more especially sulpho ethyl (meth)acrylate, 2-acrylamido-2-methyl propane sulphonic acid, allyl ether sulphonic acid and vinyl sulphonic acid.

Examples of olefinically unsaturated monomers which are free from hydroxy, sulpho and carboxy groups include 1,3-butadiene, isoprene, styrene, divinyl benzene, acrylonitrile, methacrylonitrile, vinyl halides (e.g. vinyl chloride), vinylidene halides (e.g. vinylidene chloride), vinyl esters (e.g. vinyl acetate, vinyl propionate and vinyl laurate), (meth)acrylamides, heterocyclic vinyl compounds, alkyl esters of monolefinically unsaturated dicarboxylic acids (e.g. di-n-butyl maleate and di-n-butyl fumarate) and esters of acrylic acid and methacrylic acid of formula:

$$CH_2=CR^5COOR^6$$

where $R^5$ is H or methyl and $R^6$ is an optionally substituted alkyl or cycloalkyl groups of 1 to 20 carbon atoms (more preferably 1 to 8 carbon atoms) or an alkoxysilane group, examples of which are methyl acrylate, methyl methacrylate, ethyl acrylate, ethyl methacrylate, n-butyl acrylate, n-butyl methacrylate, 2-ethylhexyl acrylate, 2-ethylhexyl methacrylate, isopropyl acrylate, isopropyl, methacrylate, n-propyl acrylate, n-propyl methacrylate and various alkoxy silane functional acrylates and methacrylates; as mentioned supra $R^6$ may also be substituted and such substituents may e.g. be or include functional groups such as amino groups, olefinically unsaturated double bonds and halide atoms such as fluorine, and examples of such monomers include (t-butylamino)ethyl (meth)acrylate, allyl (meth)acrylate, 1,1,1-trifluoroethyl (meth)acrylate and hexafluoroisopropyl (meth)acrylate.

It is preferred that the hydroxy functional polymer having carboxy groups is derived from a mixture of monomers which comprise from 0.5 to 30% by weight of one or more hydroxy functional monomers (preferably 1 to 20%), from 0.5 to 50% by weight of carboxy functional monomers, (preferably 1 to 20%), and the remaining monomers making the balance to 100% are free from hydroxy, sulpho and carboxy groups.

Polymerisation of the monomers is normally effected in an aqueous medium and in particular aqueous emulsion polymerisation is used to prepare an aqueous latex of the polymer with conventional surfactants and initiators being used. The resultant latex of the polymer could be used "as is" in the composition (apart from optional dilution or concentration or the addition of coalescing solvent to assist in film formation) and can be partially or fully neutralised before use. Alternative radical polymerisation methods can be used, for example polymerisation in the bulk or in solution with subsequent dilution with water.

The condensation polymer maybe formed by condensation of a polyol and a polyacid (to give a polyester) or of a polyol (e.g neopentyl glycol, hexane diol, trimethylol propane, glycerol) and polyisocyanate (to give a polyurethane) or of a polyol, polyester, polyacid and polyisocyanate (to give a polymer having ester and urethane groups).

The hydroxy functional polyurethane polymers having carboxy and/or sulpho groups maybe prepared by known methods, for example as described in Canadian patent application CA2059420, U.S. Pat. No. 5,194,487 and PCT application WO 92/16576. As is well known polyurethane polymers (or analogous polymers such as polyurethane ureas or polyureas) are generally made by reacting an organic polyisocyanate with an organic compound containing at least two isocyanate-reactive groups, particularly a macropolyol with the optional inclusion of a low molecular weight polyol.

Two convenient routes for the preparation of hydroxy functional polyurethanes are described by P. B. Jacobs and P. C. Yu in J. Coatings Technology, 65, No. 822, July 1993. One route involves reacting an isocyanate reactive material with a deficiency of isocyanate, for example a polyisocyanate is reacted with an excess of polyester diol and/or polyol and dimethylol propionic acid (DMPA) to produce a hydroxy terminated polyurethane oligomer having a carboxy group. A second route involves reacting a polyisocyanate, a polyol and DMPA to give an isocyanate terminated polymer which is reacted with an amino alcohol to give a hydroxy functional polyurethane polymer having a carboxygroup. Analogous routes maybe used to give hydroxy functional polyurethanes having carboxy and/or sulpho groups.

Functional groups other than carboxy and sulpho maybe present or absent from the hydroxy functional polymer, for example phosphato groups.

Polyester polymers having carboxy and hydroxy functionality maybe prepared by methods known in the art. Methods include reacting a hydroxy functional monomer and a monomer having at least two carboxy groups, and stopping the reaction before it is complete. Alternatively one may react a hydroxy functional monomer with a carboxy functional monomer in the presence of a sterically hindered carboxy functional monomer, for example dimethylol propionic acid. The latter method may also be used to give sulpho functionality by replacing the sterically hindered carboxy functional monomer with a sulpho functional monomer, for example sulphonated isophthalic acid.

Hybrid polymers having both hydroxy and carboxy functionality may also be used as component (b) of the composition. Such hybrids can be prepared by a number of methods including:

(a) polymerising a hydroxy functional monomer in the presence of a carboxy functional polymer, (b) polymerising a carboxy functional monomer in the presence of a hydroxy functional polymer, (c) polymerising a hydroxy functional monomer and/or a carboxy functional monomer in the presence of a polymer having both hydroxy and carboxy functionality, (d) polymerising a hydroxy functional monomer and a carboxy functional monomer in presence of a polymer having neither hydroxy or carboxy functionality, and (e) polymerising monomers which are free from hydroxy and carboxy groups in the presence of a polymer having both hydroxy and carboxy functionality.

The polymers referred to in (a), (b), (c), (d) and (e) above are preferably polyurethanes or polyesters. Usually the polymerisation method for forming hybrid polymers is free radical polymerisation process, and the hydroxy functional monomers and carboxy functional monomers are olefinically unsaturated hydroxy functional monomers and olefinically unsaturated carboxy functional monomers respectively, especially those described earlier in this specification.

In the case of free radical polymerisation of a hydroxy functional monomer or carboxy functional monomer in the presence of a polymer there is normally present one or more olefinically unsaturated monomers which are free from carboxy and hydroxy groups.

In one embodiment the composition is free from photoinitiators.

The sulpho and carboxy groups maybe in the free acid or salt form, preferably in salt form.

The composition maybe used as aqueous coating compositions to give films and coatings of excellent properties, and in particular excellent solvent resistance. For this purpose they maybe used "as is" or further diluted with water and/or organic solvents, or they maybe supplied in more concentrated form by evaporation of water and/or organic components of the liquid medium. As coating compositions, they maybe applied to a variety of substrates including wood, paper, cardboard, metals, glass, cloth, leather, concrete, paper, plastics, foam and the like, by any conventional method including brushing, dipping, flow coating, spraying, and the like. The liquid carrier phase is removed (drying) at elevated or even at ambient temperature, to form a film or coating. If desired the resultant film or coating can be heated at moderately elevated temperatures to accelerate the cross linking, although very often merely ageing the coating at ambient temperatures will be sufficient to develop excellent crosslinking. The compositions may contain other conventional ingredients, including organic coalescing solvents, pigments, dyes, emulsifiers, surfactants, thickeners, heat stabilisers, levelling agents, wetting agents, anti-cratering agents, fillers, sedimentation inhibitors, fire retardants, UV absorbers, antioxidants and the like introduced at any stage of making the composition or subsequently.

The compositions may also be formulated as paints, adhesives or used as binders for printing inks or as over-print lacquers, varnishes and sealants.

The present invention also provides a film and a substrate coated by a film wherein the film is obtained or obtainable by evaporation of water from the composition according to the present invention. The preferred substrates are as described above.

The MEK rub resistance test described in the examples assesses the solvent resistance of a film derived from a composition cast on a glass substrate and cured under the conditions indicated. A rag soaked in MEK is rubbed on the film to and fro until the film fails (i.e. is showing through) and the number of double rubs is recorded. If the film is still present by 200 double rubs it is rated as follows:

200 (0/5) film just failed 200 (1/5) film is severely affected 200 (2/5) film is affected 200 (3/5) film is slightly affected 200 (4/5) film is hardly affected 200 (5/5) film is unaffected The present invention is now illustrated by the following examples. Unless otherwise specified, all parts and percentages are by weight.

The following abbreviations are used in the Examples:

AA=acrylic acid
BA=butylacrylate
HEA=hydroxyethylacrylate
MAA=methacrylic acid
MMA=methylmethacrylate
MEK=methylethylketone
APTMS=3-aminopropyltrimethoxysilane
APS=ammonium persulphate
Akyposal=sodium lauryl sulphate /9278R

EXAMPLE 1

Preparation of an epoxy compound of the formula:

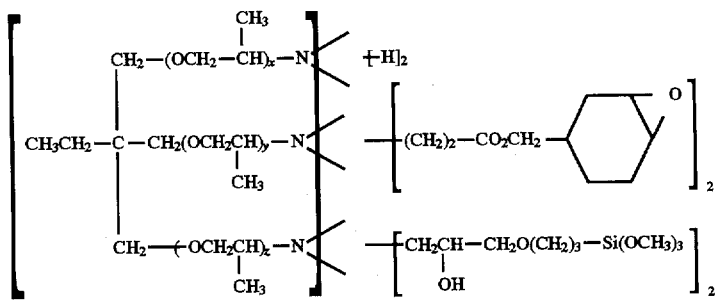

wherein x+y+z is from 5 to 6.

2,3-epoxycyclohexylmethylacryclate (0.2 moles) was added to a solution of Jeffamine T403 (40.59, 0.5 mol) in CH$_2$Cl$_2$ (35 cm$^3$) and methanol (25 cm$^3$). After 24 hours 0.2 moles of a compound of the formula:

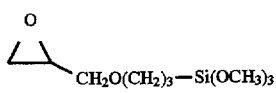

was added portionwise at 20° C. After 4 weeks standing the reaction was 95% complete and gave the title product, having three basic nitrogen atoms, two alicyclic epoxy groups and two hydrolysable silyl groups.

Jeffamine T403 can be represented by the following formula in which x+y+z=~5.3:

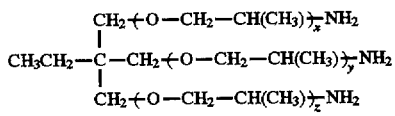

(C.A.S. Registry No. 39423-51-3).

EXAMPLE 2

Preparation of

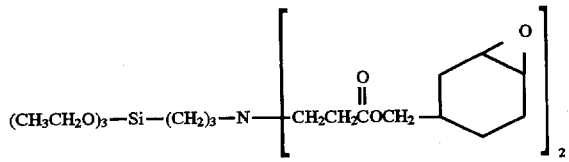

2,3-Epoxycyclohexylmethacrylate (36.49) was added to a stirred solution of 3-aminopropyltriethyoxysilane (22 g) in CH$_2$Cl$_2$ (50 ml). After 6 days stirring at room temperature the solvent was removed in vacuo to give the title product, which contains one basic nitrogen atom, two alicyclic epoxy groups and one hydrolysable silyl group, as a yellow oil.

EXAMPLE 3

Preparation of

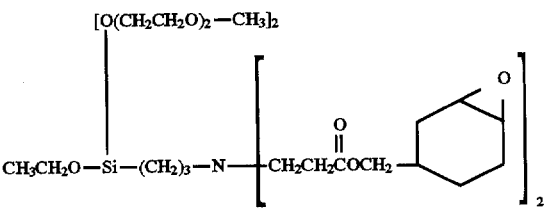

Methoxyethoxyethanol (0.4 moles) was added to 3-aminopropyltriethoxy silane (0.2 moles) and the mixture was heated at 130° C. for 3 hours. The mixture was cooled and CH$_2$Cl$_2$ (75 ml) added, followed by 2,3-epoxycyclohexylacrylate (0.4 moles). When no unsaturation was detected by $^1$H-NMR the solvent was removed in vacuo to give the title product, which contains one basic nitrogen atom, two alicyclic epoxy groups and one hydrolysable silyl group, as a yellow viscous oil.

EXAMPLE 4

Preparation of further epoxy compounds
Preparation I

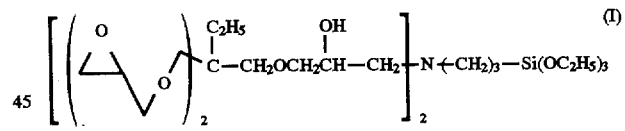

To trimethylolpropanetriglycidylether (4.5 g, "Heloxy 5048" ex Hi-Tek Polymers. Epoxide wt=145–165) was added 3-aminopropyl triethoxysilane (1.1 g); Epoxide:active NH 3:1. After 3 days at ambient temperature the ratio of epoxide groups to silicon was shown by NMR to be 2:1 corresponding to the above formula.
Preparation II

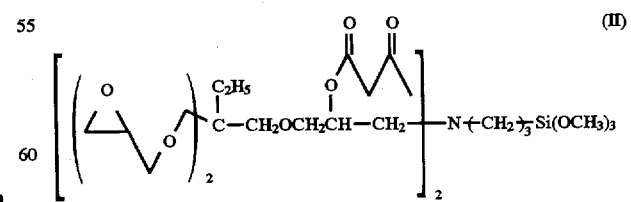

APTMS (11.1 g) was added to a solution of Heloxy 5048 (45 g) in dry CH$_2$Cl$_2$ (50 ml). After the exotherm had subsided the mixture was left at room temperature for 18 hours, then treated with freshly distilled diketene (8.4 g) and dimethylaminopyridine ("DMAP", 0.001 g). After a further 10 hours the solvent was evaporated to give the title product as a yellow oil.

Preparation III

The method for preparation of I was followed except that in place of the 4.5 g of Heloxy 5048 there was used 3.0 g. The resultant compound, named Preparation III, was less storage stable than Preparation I and gelled after a few days.

Preparation IV

To a 2 day old sample of Preparation III (4.1 g) was added diketene (0.84 g) and a catalytic amount of DMAP. The product, namely Preparation IV, was found to be storage stable.

Preparation V

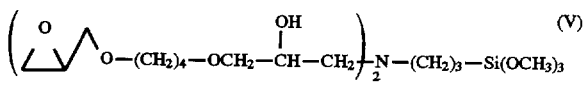 (V)

To butanedioldiglycidylether (20 g, 0.1M) was added APTMS (11.0 g, 0.05M) to give the title product having an initial epoxide to active NH ratio of 2:1. After 2 days at room temperature the product was found relatively unchanged. After 6 days the product had gelled.

Preparation VI

Preparation V was treated with diketene in an analogous manner to that described in Preparation II above. The resultant product, namely Preparation VI, was found to be storage stable.

Preparation VII

To APTMS (35.8 g, 0.2M) was added vinylcyclohexene-dioxide (28 g, 0.2M). The mixture was warmed to 50° C. for 18 hours after which all the primary amine had reacted. The product gelled after 2 months.

Preparation IX

 (IX)

APTMS (17.9 g) was added dropwise, with stirring over 15 minutes, to ice-cooled glycidylacrylate (12.9 g). After 2 hours, NMR indicated that the title preparation IX had been formed. Preparation IX was found to be stable for a few hours.

Preparation X

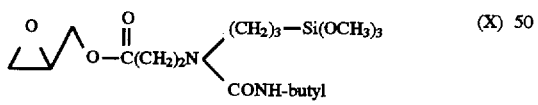 (X)

Butylisocyanate (9.9 g) was added to a cold fresh solution of Preparation IX. After 2 hours title Preparation X had been formed and was found to be storage stable.

Preparation XI

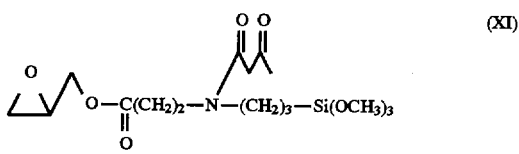 (XI)

Preparation IX (30.8 g) was treated dropwise with diketene (8.4 g) to give the title Preparation XI.

Preparation XII

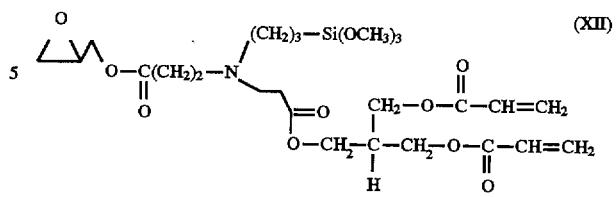 (XII)

To a fresh sample of Preparation IX was added 1 equivalent of TMPTA (Trimethylolpropanetriacrylate) (a three fold excess of acrylic groups to —NH—group) to give the title product as a storage stable liquid.

Preparation XIII

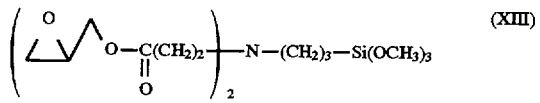 (XIII)

APTMS (8.84 g, 0.045M) was added a solution of glycidyl acrylate (13 g, 0.1M) in dry $CH_2Cl_2$ (15 ml). The temperature rose to 33° C. and the mixture was stood for 3 days, after which unsaturation had reduced to a steady value equivalent to 80% conversion of starting materials to title preparation. A further portion of APTMS (2 g) was added. After 1 month the product had gelled.

Preparation XIIIA

Preparation XIII was reacted with butylisocyanate to give Preparation XIIIA.

Preparation XIIIB

Preparation XIII was reacted with diketene to give Preparation XIIIB.

Preparation XIV

Isophorone diisocyanate (11.0 g) was added dropwise with stirring to a solution of Preparation IX (30.8 g) in dry $CH_2Cl_2$ (50 ml) at 0°–5° C. After standing for 16 hours the $CH_2Cl_2$ was removed in vacuo to give preparation XIV as a clear viscous oil.

Preparation XV

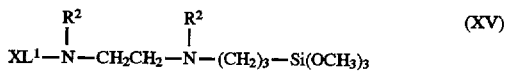 (XV)

wherein one $R^2$ is H and the other $R^2$ is —$L^1X$ where —$L^1X$ has the formula:

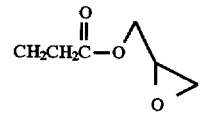

$H_2NCH_2CH_2NH(CH_2)_3$—$Si(OCH_3)_3$ (22.2 g) in dry $CH_2Cl_2$ (50 ml) was added over ½ hour, with stirring, to a solution of glycidyl acrylate (25.6 g) in dry $CH_2Cl_2$ (50 ml) at 0° C. After 5½ hours NMR indicated the formation of Preparation XV having very low residual unsaturation.

Preparation XVA

Preparation XV (23.9 g) was reacted with butylisocyanate (5 g) to give preparation XVA, having the formula XV shown above but with a —CO—NH—Butyl group in place of the hydrogen atom represented by $R^2$.

Preparation XVB

Preparation XV (23.9 g) was reacted with diketene (4.3 g) to give preparation XVB, having the formula XV shown above but with a —$COCH_2COCH_3$ group in place of the hydrogen atom represented by $R^2$.

Preparation XVI

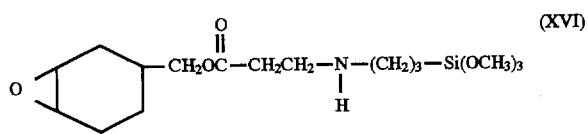

2,3-Epoxycyclohexylmethylacrylate (125 g, "Cyclomer A200", available from Diacel) was added over 30 minutes to APTMS (123 g). After 1 day stirring the title preparation XVI was isolated and found to be storage stable.

Preparation XVII

Preparation XVI was reacted with one equivalent of diketene at 20°–25° C. to give preparation XVII.

Preparation XVIIA

Preparation XVI was reacted with one equivalent of butylisocyanate to 20°–25° C. to give preparation XVIIA.

Preparation XVIII

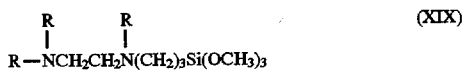

APTMS (17.9 g, 0.1M) was added to a solution of Cyclomer A200 (36.4 g, 0.2M) in $CH_2Cl_2$ (50 ml) and methanol (10 ml). After 3 days NMR indicated that the reaction was complete giving preparation XVIII as a storage stable material.

Preparation XIX $$R—NCH_2CH_2N(CH_2)_3Si(OCH_3)_3 \quad (XIX)$$

wherein one R is H and two groups represented by R are of the formula:

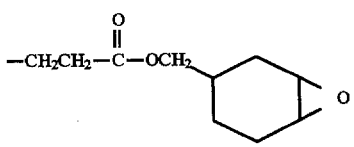

Cyclomer A200 (0.1M) was added dropwise with stirring to $H_2NCH_2CH_2NH(CH_2)_3Si(OCH_3)_3$ (0.2). After standing at room temperature for 1½ days NMR indicated that the title preparation XIX had been formed. Preparation XIX was found to be storage stable.

Preparation XX

Preparation XX was made according to the method described in Example 6, Stage a).

Preparation XXI

The method described above for Preparation XV was followed except that in place of glycidyl acrylate there was used 2,3-epoxycyclohexylacrylate. The product, namely Preparation XXI, was obtained as a storage-stable pale yellow liquid.

Preparation XXII

The method described for Preparation XV was followed, except that in place of $H_2NCH_2CH_2NH(CH_2)_3—Si(OCH_3)_3$ there was used $H_2NCH_2CH_2NH(CH_2)_3—SiCH_3(OCH_3)_2$, to give preparation XXII.

Preparation XXIII

Methyl polyethylene glycol methacrylate (0.04M, 25.4 g, available from B.P. Chemicals as MPEG 550 MA) was added to $H_2NCH_2CH_2NH(CH_2)_3—Si(OCH_3)_3$ (0.2M, 44.4 g) and the mixture stirred for 2 days at 52° C. Glycidyl acrylate (0.34M, 43.5 g) was added at room temperature over 30 minutes. The temperature rose to 30° C. and the mixture was maintained at 30° C. for 6 hours, cooled to 10° C. and treated with butyl isocyanate (0.2M, 19.8). The resultant product was found to be dispersible in water.

EXAMPLE 5

Preparation and Comparison of hydroxy functional polymers having Carboxy groups with polymers having only Carboxy Functionality Step a)

A polymer having carboxy and hydroxy functionality was prepared as follows (hereinafter the "OH+COOH polymer").

A 1 liter round bottom flask was fitted with a stirrer, dropping funnel and thermometer was purged with nitrogen gas. A solution of Akyposal 9278R surfactant (7.4 g of a 30% strength solution in deionised water) in water (280 ml) was added to the flask. An emulsion comprising water (112 g), MAA (14.6 g), HEA (19.6 g), MMA (138 g), BA (155 g), Akyposal 9278R (22 g of a 30% strength solution in deionised water) and APS (1.64 g) was charged into the dropping funnel. Approximately 10% of the dropping funnel contents was added to the flask and the flask was then headed to 85° C. The remaining contents of the dropping funnel were added dropwise over 1.5 hours and the flask was heated at 85° C. for a further 1 hour. The flask contents were filtered and the filtrate cooled to give the OH+COOH polymer as a low viscosity white emulsion having a solids content of about 44%.

Step b)

Preparation of a polymer having carboxy groups and no hydroxy groups (hereinafter the "carboxy polymer"). A carboxy polymer was prepared in a similar manner to Step a) except that an emulsion was used comprising MAA (4.45%), MMA (46.6%) and BA (48.9%).

Step c)

Evaluation

The polymers described in Steps a) and b) were adjusted to pH 6.8 and treated with the cross-linker preparations mentioned in the first column of Table 1. The second column states the amount of preparation used (weight % relative to the polymer).

TABLE 1

| Prepa-<br>ration | Wt % of<br>Preparation<br>to polymer | Polymer | CURE/MEK RUB RESISTANCE | | |
|---|---|---|---|---|---|
| | | | 1 day<br>RT | 2 days<br>RT | 5 days<br>RT |
| XVA | 7.2 | OH + COOH | 200(3) | 200(5) | — |
| XIIIA | 4.0 | OH + COOH | 200(4) | 200(5) | — |
| XIIIA | 4.0 | Carboxy | 100–200 | 200(2) | — |
| XVIII | 5.4 | OH + COOH | 40–50 | 200(0) | 200(4) |
| XVIII | 5.4 | Carboxy | <20 | 30–40 | 50–60 |
| XXI | 5.0 | OH + COOH | 90 | — | 200(4) |
| XXI | 5.0 | Carboxy | 20–30 | — | 40–50 |
| A187 | 5.5 | OH + $CO_2H$ | 120 | 200(3) | 200(4) |
| A187 | 5.5 | Carboxy | <20 | 25–30 | 25R |
| None | — | OH + $CO_2H$ | <20 | <20 | <20 |
| None | — | Carboxy | <20 | <20 | <20 |

A187 is glycidylpropyltrimethoxysilane:

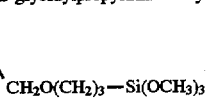

Table 1 shows that compositions comprising the crosslinker preparations and a polymer having both carboxy and hydroxy functionality have higher MEK rub resistance than compositions where the polymer has only carboxy groups.

We claim:

1. A composition comprising water and the following components:
   a) an epoxy compound comprising at least one epoxy group, at least one nitrogen atom selected from the group consisting of amino, amido and urea nitrogen atoms and at least one hydrolysable silyl group; and
   b) a hydroxy functional polymer having carboxy and/or sulpho groups.

2. A composition according to claim 1 wherein component (a) is of Formula (1):

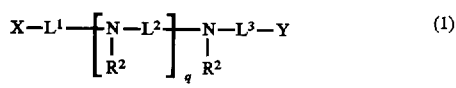

wherein:

X is $E-(L^4-O)_m-(CO)_n-(T)_p-$;

Y is $-Si(R^1)_3$ wherein each $R^1$ independently is optionally substituted alkyl or optionally substituted alkoxy provided at least one $R^1$ is optionally substituted alkoxy;

T is O, $CH_2$ or $NR^2$;

p is 0 or 1;

q is 0, 1, 2, 3 or 4;

E comprises an epoxy group;

each $L^1, L^2, L^3$ and $L^4$ independently is a divalent organic linker group;

m and n are each independently 0 or 1; and each $R^2$ independently is H $L^1X$ or optionally substituted alkyl or acyl.

3. A composition according to claim 1 wherein component (a) is of Formula (2)

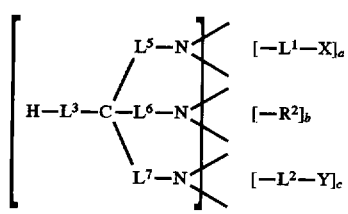

wherein:

$L^1, L^2, L^3$, and Y are as defined in claim 5;

$R^2$ is H or optionally substituted alkyl or acyl;

$L^5, L^6$ and $L^7$ are each independently organic linker groups;

a is 1 to 5;

b is 0 to 4;

c is 1 to 5; and (a+b+c)=6.

4. A composition according to claim 1 wherein component (b) is a hydroxy functional polymer having carboxy groups.

5. A composition according to claim 1 wherein component (b) is a hydroxy functional polymer having sulpho groups.

6. A composition according to claim 1 wherein component (b) is a hydroxy functional polymer having carboxy and sulpho groups.

7. A composition according to claim 4 wherein component (b) is an addition polymer.

8. A composition according to claim 4 wherein component (b) is a condensation polymer.

9. A film or coating obtained or obtainable by evaporation of water from a composition according to claim 1.

10. A composition according to claim 2 wherein in component (a) q is 1 and $L^2$ is $(CH_2)_2$ which reduces to the formula:

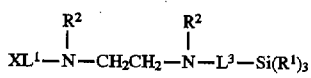

wherein $L^3$ is a divalent organic linker group, each $R^1$ independently is $C_{1-4}$-alkyl or $C_{1-4}$-alkoxy, provided at least one $R^1$ is $C_{1-4}$-alkoxy; and wherein further $R^2$ is H, $-L^1X$ or $-CONH(C_{1-4}$-alkyl) provided that one $R^2$ is H or $-CONH(C_{1-4}$-alkyl) and the other $R^2$ is $-L^1X$ where X has $L^4=CH_2$, m=1, and E is of formula (ii) and $L^1$ is $(CH_2)_2$, which reduces $-L^1X$ to the formula:

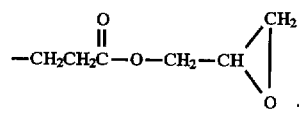

11. A composition according to claim 2 wherein in component (a) q is 1, $L^2$ is $(CH_2)_2$ and $L^3$ is $(CH_2)_3$, which reduces to a compound of the formula:

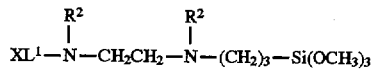

and wherein further one $R^2$ is $-CO-NH$-butyl and the other $R^2$ is $L^1X$ where X has $L^4=CH^2$, m=1, and E is of formula (ii) and $L^1$ is $(CH_2)_2$, which reduces $-L^1X$ to the formula:

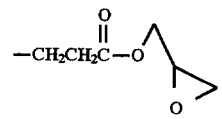

and (b) is a hydroxy functional polymer having carboxyl groups.

* * * * *